(12) United States Patent
Rasche et al.

(10) Patent No.: US 6,619,840 B2
(45) Date of Patent: Sep. 16, 2003

(54) INTERVENTIONAL VOLUME SCANNER

(75) Inventors: Volker Rasche, Hamburg (DE); Joern Luetjens, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 32 days.

(21) Appl. No.: 09/978,115

(22) Filed: Oct. 15, 2001

(65) Prior Publication Data

US 2003/0072416 A1 Apr. 17, 2003

(51) Int. Cl.⁷ ................................................ H05G 1/02
(52) U.S. Cl. .......................................... 378/197; 378/196
(58) Field of Search ................................ 378/187, 198, 378/196, 193, 197, 17

(56) References Cited

U.S. PATENT DOCUMENTS

| | | | | |
|---|---|---|---|---|
| 3,549,885 A | * | 12/1970 | Anderson | 250/65 |
| 6,104,780 A | * | 8/2000 | Hanover et al. | 378/92 |
| 6,113,264 A | * | 9/2000 | Watanabe | 378/197 |
| 6,203,196 B1 | * | 3/2001 | Meyer et al. | 378/197 |

* cited by examiner

Primary Examiner—Drew A. Dunn
Assistant Examiner—Irakli Kiknadze
(74) Attorney, Agent, or Firm—John Vodopia

(57) ABSTRACT

A C-arm X-ray system is disclosed which includes an X-ray source, an X-ray detector and a support C-arm mechanism including an outer and inner C-arm. The X-ray source and the X-ray detector are oppositely disposed on the inner C-arm. The inner C-arm is suspended upon at least one wheel construction disposed in the support C-arm. The inner C-arm may be automatically driven annularly outside of a first end of the C-arm support and into a second end of the C-arm support to close a gap normally found in conventional C-arm X-ray devices. Such construction allows the X-ray source and X-ray detector to rotate at least one full 360 degree cycle, providing an C-arm X-ray device capable of performing both fluoroscopic and CT procedures without a need to move a patient under examination (i.e., monitoring the patient in a common frame of reference for both applications).

15 Claims, 8 Drawing Sheets

INTERVENTIONAL VOLUME SCANNER

BACKGROUND OF THE INVENTION

The invention relates to C-arm X-ray systems, and more particularly to a C-arm X-ray system with full volume imaging capability for use in interventional procedures.

Various C-arm X-ray devices and system are known in the art. For example, German patent No. DE 198 39 825 C1 ("the '825 patent"), incorporated herein by reference, discloses an X-ray device in FIG. 1A comprising circular support equipment 1. The circular support equipment includes a C-shaped arm or first ring segment 4. The first ring segment 4 is attached to the circular support equipment 1 via a first bearing equipment 9 and further includes an X-ray source 2 and an X-ray detector 3 disposed at opposing sides of a patient 7. The X-ray device of the '825 patent also includes a second ring segment 5 attached to second bearing equipment 12 and head lining rail 13.

The circular support equipment 1, first bearing equipment 9, first ring segment 4, X-ray source 2 and detector 3 of the '825 patent device may be used to perform conventional fluoroscopy. The second ring segment 5 may be pivoted about a tangential pivot axis to bring the second ring segment 5 into alignment with the first ring segment 4. This allows (when attached and aligned) 360 degree rotation of the X-ray source 2 and detector 3 about the patient 7. Hence, the '825 patent devices include an ability to operate as a computer tomography device as well as a conventional C-arm type fluoroscope.

The '825 patent device has its limitations, however. In particular, the second ring segment 5 must be mechanically aligned, brought into contact with, and plugged into (attached to) the first ring segment 4 before the CT mode of operation may be implemented. This requires that a mechanical tenon 28 which fits into a mortise 29 constructed within the second ring segment 5, as shown in FIG. 1A.

A bolt 30 is inserted into a bolthole of at least one mechanical tenon 28 in order to lock the first and second ring segments. As such, making the connection requires substantial effort in both the alignment and the locking together of the ring segments.

Moreover, the head lining 13, the second bearing equipment 12 and berth the equipment 6 take up a substantial volume which is certainly a hindrance to the technical individuals who would utilize the construction to perform both conventional fluoroscopic and CT scanning during an interventional medical procedure. The patient 7 is difficult to access in particular positions because of the structure itself, and the necessary elements required to lock the first and second ring segments.

The '825 patent also includes two additional proposals for realizing the closed circle (ring) with its inherent ability to rotate a full 360 degrees. That is, the '825 patent also includes an embodiment which uses two (2) interleaved c-shaped arcs (FIGS. 5–11).

Another embodiment of the '825 patent is constructed to use two (2) c-shaped arcs connected vertically utilizing a hinge.

Each of the above-mentioned embodiments (i.e., the three (3)-introduced approaches) aim for the generation of a rigid circle or ring that can be used for performing 360° rotations. The basic idea is to use the standard support of the C (16 in FIG. 1 of the '825 patent) and simply increase the range of the rotation of the c-shaped connection between tube and detector (4, FIG. 1 of the '825 patent) from 180 (FIG. 1) to 360° (FIGS. 2, 7, 10, 11, and 14).

The tube and detector are supported either on two sides (FIG. 2) or on a single side only (rest). Where the first embodiment of the '825 patent is limited to rotation of the tube-detector-ensemble around the patient axis (table axis), the second and third embodiments mentioned above basically provide a full 360 degrees of freedom (of course within the limitations given by the patient). That is, by allowing a choice of allowing the rotation axis to rotate the support of the closed circle or ring (16) around the horizontal rotation axis (10) or even the vertical rotation axis (11) allow for 360 degrees of freedom.

Where the first-mentioned embodiment requires additional space-consuming equipment (5, 14, 13, 15), solutions 2 and 3 (at least to a certain extent) do not require significant additional equipment. Hence, in fluoroscopic mode, the systems are almost equal to a fluoroscopic-only system from an applicational (functional) point of view. The major drawback of all solutions suggested taught by the '825 patent is the need for rebuilding the system when switching between fluoroscopic and CT mode, and vice versa.

OBJECTS AND SUMMARY OF THE PRESENT INVENTION

Accordingly, it would be desirable for those skilled in the art to realize a C-arm type X-ray system in which a second C-arm element is available for closing the gap in the primary or support C-arm to form a closed ring which overcomes the shortcomings of prior art C-arm X-ray systems, e.g., the '825 patent.

It is therefore an object of the present invention to provide a C-arm X-ray system which supports full volume imaging capabilities with the full flexibility required for interventional procedures without a need to rebuild the system when switching between fluoroscopic and CT modes of operation.

It is another object of the invention to provide a C-arm X-ray system in which an inner "C" of a C-arm mechanism may be enabled and guided by an outer "C" to allow for 360 degree rotation of oppositely disposed X-ray source and X-ray detector mounted on the inner C-arm of the C-arm mechanism. The construction allows operation without the need for a conventional rigid C-arm support, such as that described in the prior art '825 patent.

It must be noted that the inner "C" is never fixed to the support "C", even when at rest. The use of the terms "stable", "closed ring" etc. are not meant to imply that the inner C-arm is affixed to the support C-arm. That is, the two "C's" themselves possess the possibility to perform a 360° rotation without the need to construct an auxiliary closed ring beforehand.

It is another object of the invention to provide a C-arm X-ray system that can provide a simple and elegant method of obtaining X-ray projections of a patient from any direction without having to move the patient.

It is another object of the invention to provide a C-arm X-ray system that can provide a simple and elegant method of switching between CT and fluoroscopic applications (e.g., angiographic), without moving the patient from one device to another.

It is another object of the invention to provide a C-arm X-ray system which provides a simple and elegant method of switching between CT and fluoroscopic applications (e.g., angiographic), while maintaining the patient in a common frame of reference (coordinate system) relative to a gantry (comprising the system). Consequently, acquisition of data from both applications allows the combined data to realize additional, previously unavailable diagnostic information, as well as easy patient access during an interventional procedure.

It is another object of the invention to provide a C-arm X-ray system in which a first support C-arm (e.g., 210 degree arc length) including an inner C-arm (e.g., at least 150 degrees of arc length) which inner C-arm may be automatically extended to close the gap in the support c-arm and allow an x-ray source and oppositely disposed x-ray receiver to rotate a full 360 degrees.

The arc length of the support "C" determines the size of the gap size (360°-arc length of support "C") and hence the patient accessibility. It must be 180° plus ½ overlap with the inner "C". The inner "C" must have at least 180°, at most the same arc length as the support "C", else the gap size would decrease. In order to make the construction as rigid and stable as possible, the inner "C" should have its maximum arc length. Both arc lengths should be the same and a compromise has to be made between stability and patient accessibility. A preferred embodiment may be constructed to be about a 210° arc length for a 150° gap size.

It is another object of the invention to provide a C-arm X-ray system in which a second C-arm element, constructed within a first support C-arm, may extend from a support mechanism within the first C-arm (at a first end) to close the gap and re-enter an opposite (second) end of the first C-arm.

It is another object of the invention to provide a C-arm X-ray system in which the "C" may be extended a full 360 degrees by including and inner C-arm element which may exit/enter each opposite C-arm support by use of a particular type of driving mechanism located at each end thereon, providing an ability to utilize both CT and fluoroscopic modes of system operation without the need to rebuild the system of move the patient under examination.

It is another object of the invention to provide a C-arm X-ray system in which an inner C-arm disposed within a support C-arm may be extended a full 360 degrees (circle) from within the support C-arm with a gear rim on its outer or inner surface, the gear ring providing a means to transfer rotation of diametrically opposed X-ray source and detector mounted on the closed ring.

BRIEF DESCRIPTION OF THE DRAWING FIGURES

The above and other more detailed aspects of the invention will be described in detail hereinafter, by way of example, with reference to the following drawing figures.

DETAILED DESCRIPTION OF THE PREFERRED EMBODIMENTS

The reader should note that the embodiments described herein are for exemplary purposes only, and are not meant to limit the scope and spirit of the invention.

Figure 1A:
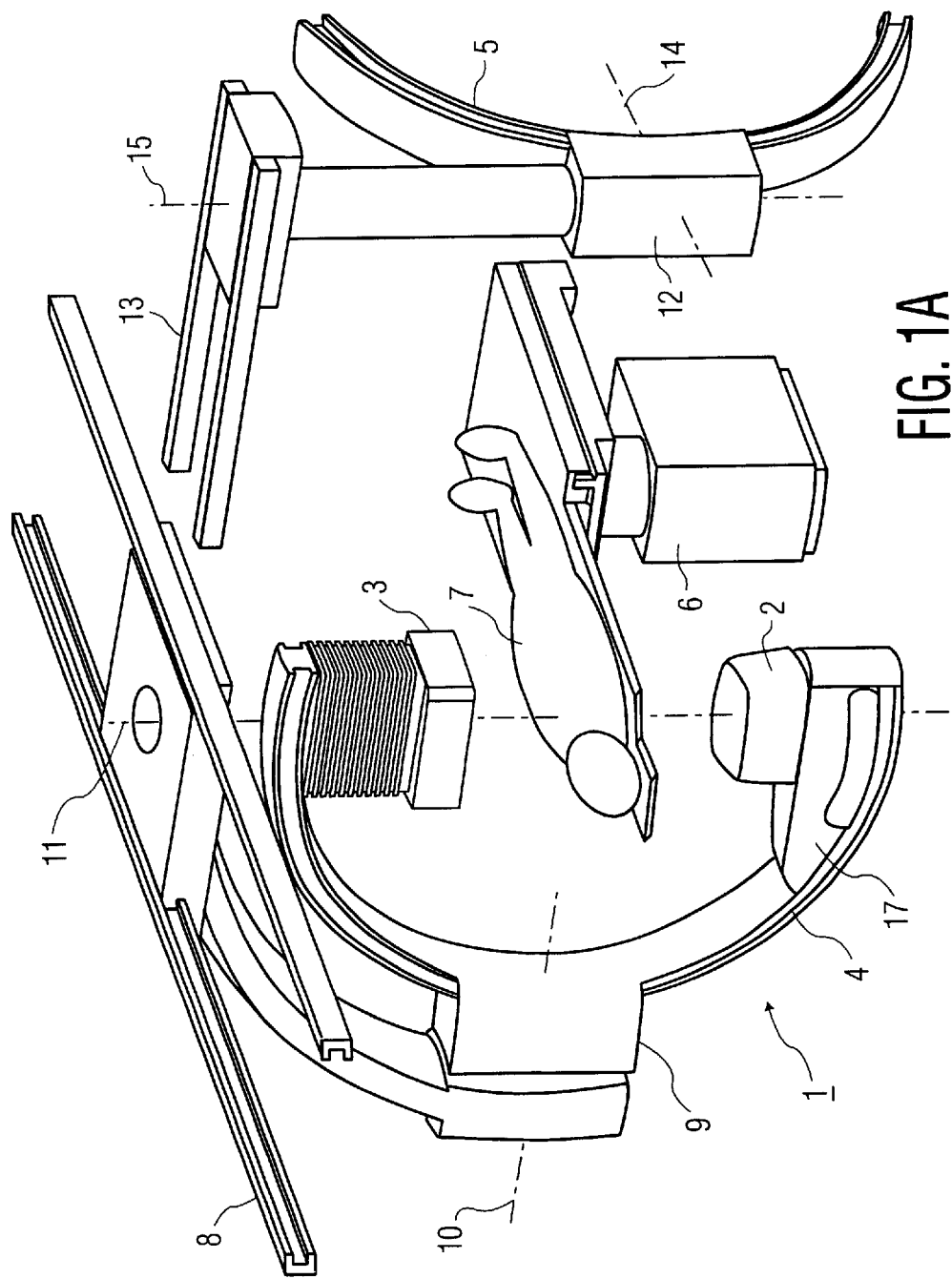
FIG. 1A is a schematic diagram of an X-ray device disclosed by prior art German Patent No. DE 198 39 825 ("the '825 patent")
Figure 1B:
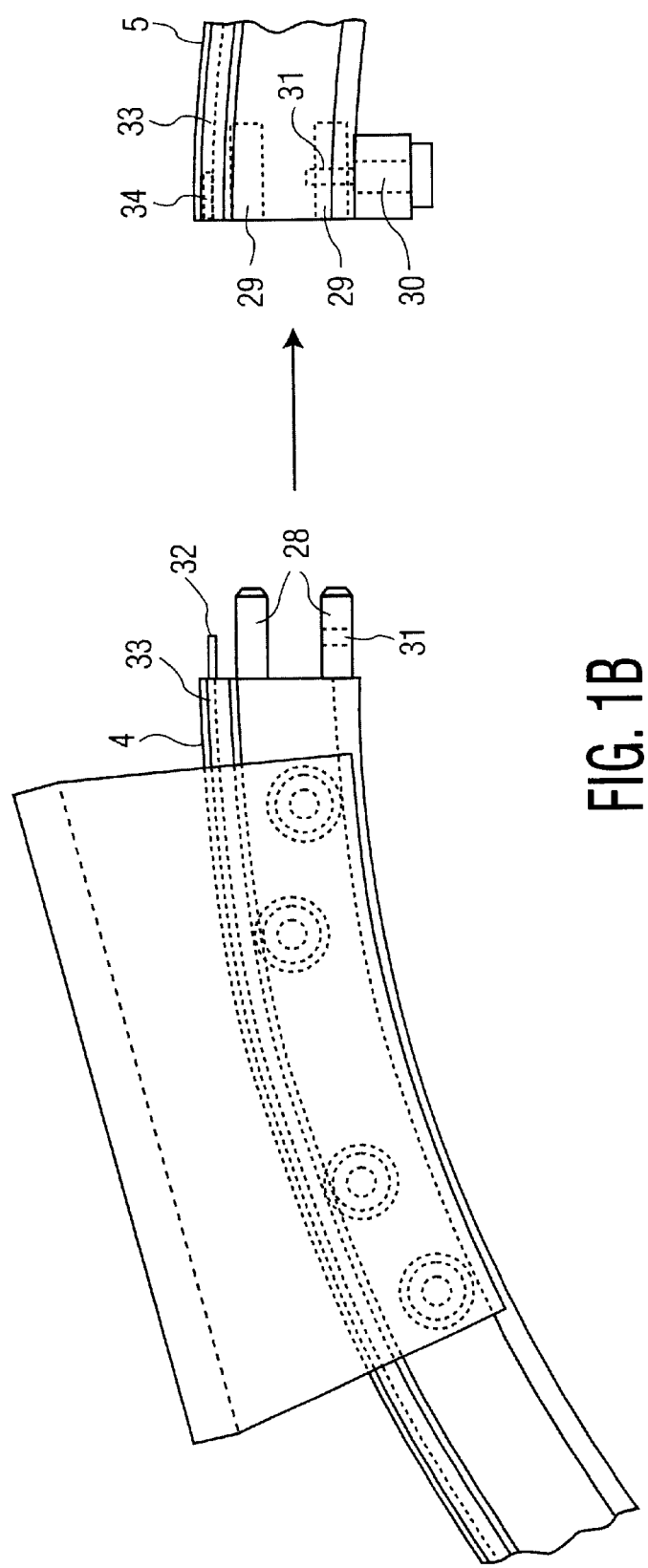
FIG. 1B is a schematic diagram of a plug and socket utilized for forming a closed ring in the X-ray device of the prior art '825 patent.
Figure 2:
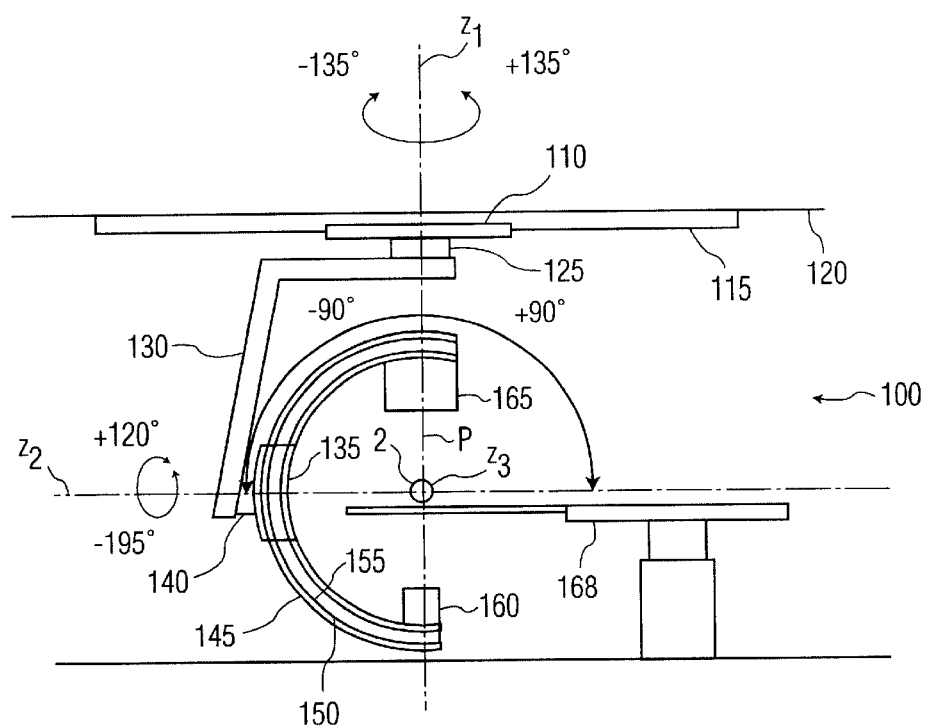
FIG. 2 is a schematic diagram of a standard off-the-shelf C-arm X-ray system.

A conventional C-arm X-ray system 100 is described in FIG. 2. C-arm X-ray system 100 includes a rail mechanism 110, 115, mounted to a mounting surface 120 and connected to a rotational element 125. The rotational element is attached to a support arm 130. Support arm 130 is connected to a bearing equipment/rail-holding system 135 via a second rotational element 140. A C-arm element 145 is attached to the bearing equipment/rail-holding system 135 and comprises an outer rail portion 150 and an inner portion 155. Inner and outer rail portions 150 and 155 depict the tracks for the 135 to hold on to. Mounted in diametrically opposing positions on the support C-arm 145 are an X-ray source 160 and X-ray detector 165 for exposing a patient on patient table 168.

In contrast to the prior art C-arm X-ray system of FIG. 2, the present invention provides for closing the gap to utilize the system in CT mode operation without a need to rebuild the system. That is, the support "C" is constructed with an inner "C" element which may be annularly extended from within the support C-arm (at a first end) to close the gap (e.g., a "C''" arc length of 150 degrees) and enter the C-arm support at its opposite end.

As seen in FIG. 2 of the prior art, the X-ray source 160 and X-ray detector 165 are arranged in a position relative to one another in such a manner that x-rays emanating from the source along the projection radius P traverse an object to be examined (e.g., a human patient) arranged on a patient table 160 (168) in the examination zone Z. The X-rays emitted are therefore incident on X-ray detector 165, and both source and detector are rotatable (e.g., 210 degrees) about the $Z_3$ axis via outer rail portion 150 of C-arm 145.

As disclosed by the '825 patent, a rigid supporting device 130 is also mounted via the second rotational element 140 to enable rotation about the $Z_1$ axis on a slide rail mechanism 110, 115, which rigid support device is displaceable in the rail mechanism. As will be understood by those of skill in this art, and as is already indicated by the angles given, the degree of freedom is limited in such prior art FIG. 2 X-ray device. Moreover, while such a conventional C-arm diagnostic X-ray system and/or device (prior art FIG. 2) provides an ability to obtain X-ray projections of a patient from any direction without having to move the patient, such is not the case for conventional CT type gantries.

Conventional CT type gantries offer CT mode applications which require a 360-degree rotation about a patient. Of course it is desirable to have a C-arm X-ray device which has a capacity to perform both CT and fluoroscopic mode operations during an interventional procedure, and to easily switch the system operating structure. That is, it is desireable to switch between these two operating modes without moving the patient from one device to another in order to derive data from both separate applications in the same patient coordinate location. Moreover, as discussed above with respect to at least the first and third mentioned embodiments of the '825 prior art patent reference, to perform an angiographic or CT mode application requires moving either the patient or the second head lining rail 13, second bearing equipment 12 and second ring segment 5 which is cumbersome and time consuming at best.

Figure 3A:
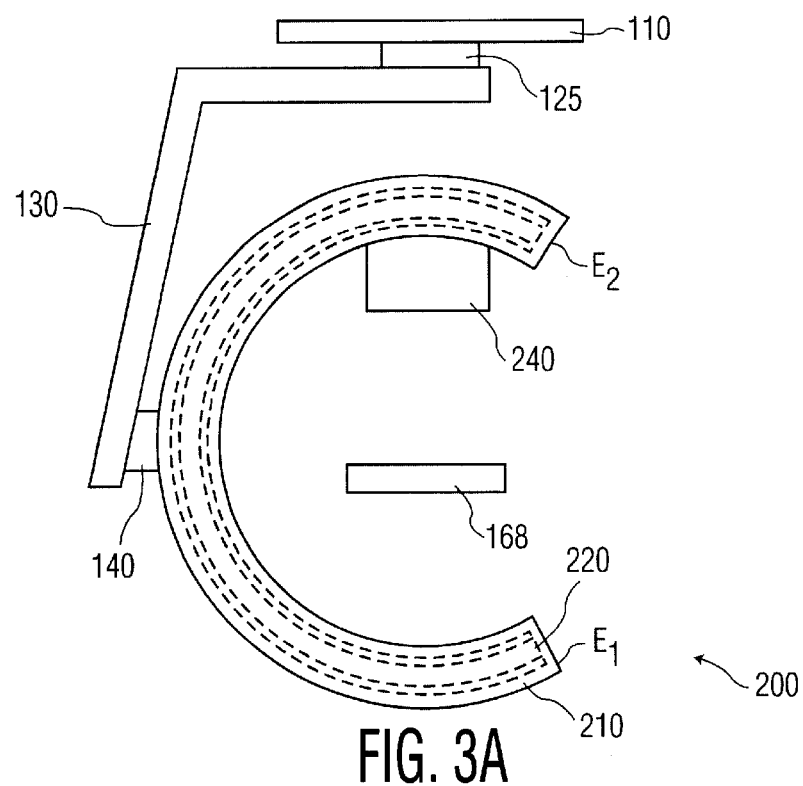
FIGS. 3A & 3B are schematic diagrams of a C-arm x-ray system constructed in accordance with the principles of this invention depicting its inner C-arm both before and after extension beyond the gap of the "C", respectively.
Figure 3B:
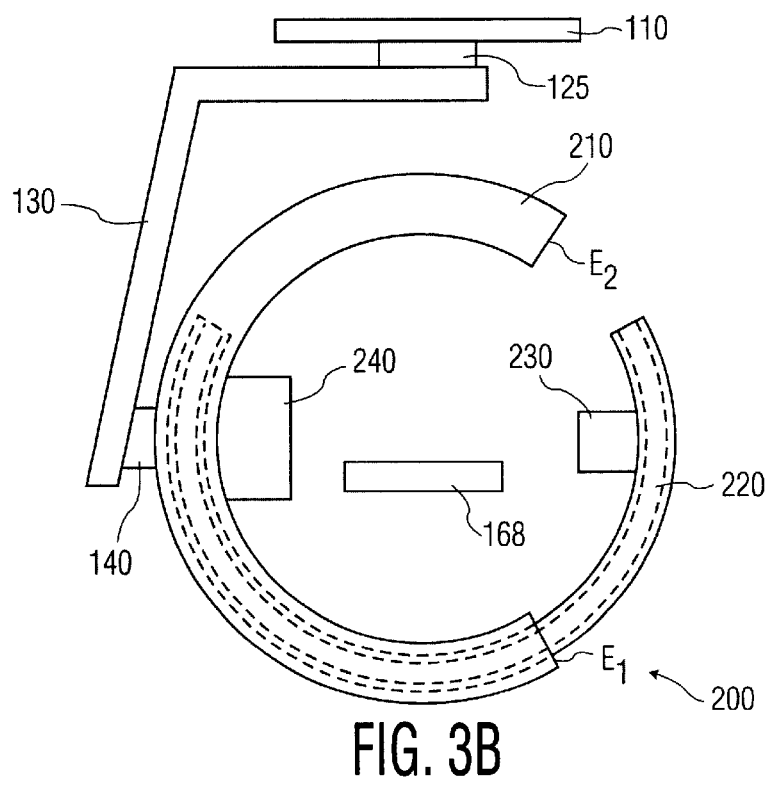

A first embodiment of applicants' interventional volume scanner C-arm X-ray system 200 is depicted in FIGS. 3A and 3B. The first embodiment is an improvement of the design of the standard or conventional C-arm x-ray system 100 (the '825 prior art patent), shown in FIG. 2. The '825 patent system is described above as including a standard C-arm x-ray system 100 equipped with three-rotation axis to provide three degrees of freedom ($Z_1$, $Z_2$ and $Z_3$). As known to those skilled in the art, during volume reconstruction, it is desirable to have at least one axis available for providing a full rotation of 360 degrees without a need for reconstructing the system to switch between operating modes or moving the patient from a fluoroscopic system to a CT mode system, or vice versa. More particularly, continuous 360-degree rotation is considered the ideal for large volume coverage along the patient (or $Z_2$) axis while maintaining the patient under examination in his/her original position without major system reconstruction.

Figure 6A:
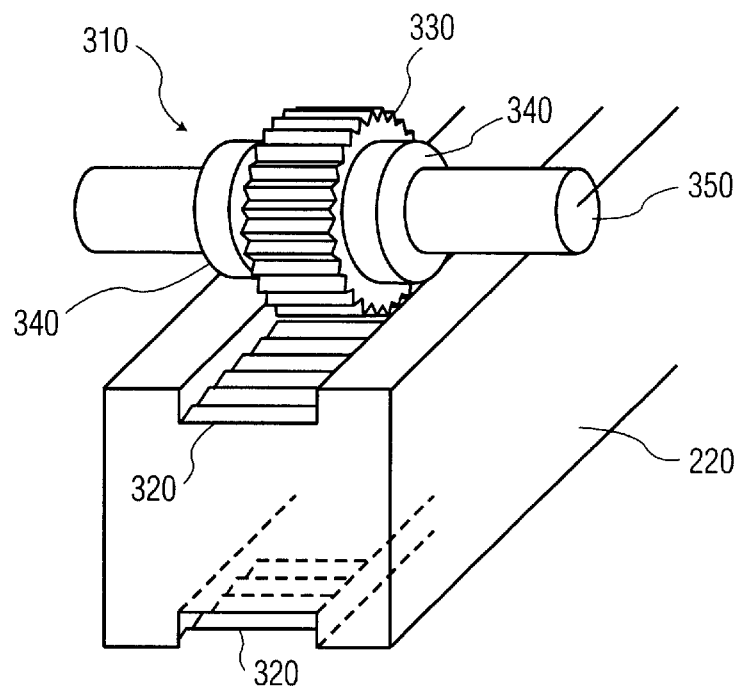
FIGS. 6A & 6B are plan views of two embodiments of wheel constructions required for stable operation of the C-arm X-ray systems of the present invention.
Figure 6B:
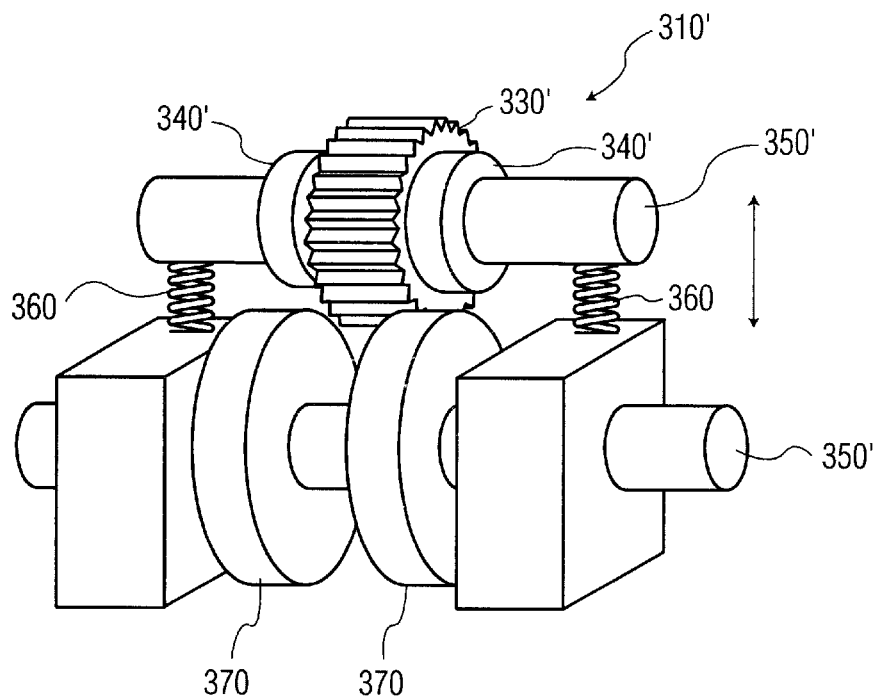
Figure 7:
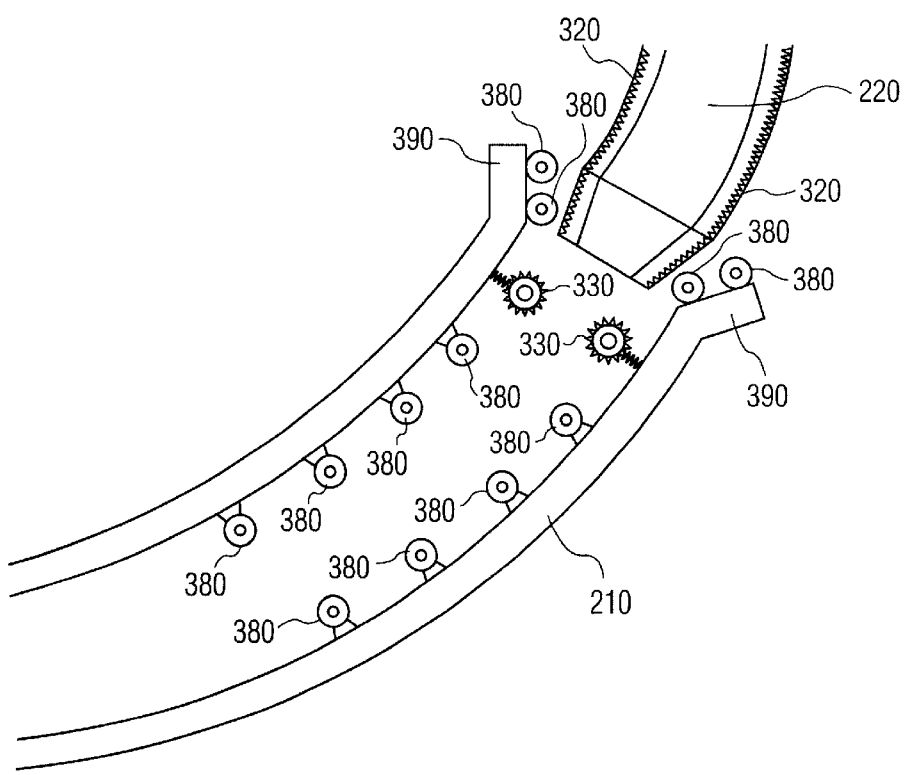
FIG. 7 is a schematic representation of a side/cut-off view of an embodiment of an entry end of a support C-arm, a tapered end of an inner C-arm, wheel constructions and cogwheels for use with a C-arm X-ray system of this invention.

C-arm X-ray system 200 comprises a C-arm mechanism including a primary or support (used interchangeably herein) C-arm 210 constructed with an inner C-arm 220 suspended on wheel constructions (shown in FIGS. 6A, 6B and 7) within the primary or support C-arm 210. One skilled in the art will understand that there must be a sufficient number of wheel constructions to provide a stable suspension for the inner C-arm 220 as it extends between a first (E1) and second (E2) end of the support C-arm 210 (i.e., at least one pair of wheel constructions and cogwheels at each end, as shown in FIGS. 6A, 6B, and 7). For that matter, the inner C-arm may travel a full 360 degrees periodically about the patient table. With every cycle, the inner C-arm must exit one end and enter the other end of the support C-arm such that a gap exists at some portion of the 360 degree period when the inner C-arm is completely enclosed by the support C-arm. A closed ring is only present for some portion of the 360 cycle.

The inner C-arm 220 is shown in a particular extended position in FIG. 3B. The inner C-arm 220 is extended from the first end (E1) of the support C-arm 210 and constructed with a sufficient arc length to contact with and enter into the second end (E2) of the support C-arm 210. A gear rim (not shown in FIGS. 3A and 3B) is constructed on the at least one side of the inner C-arm 220 and adjacent the cogwheels (see FIGS. 6A and 6B).

The C-arm X-ray system 200 shown in FIGS. 3A and 3B are exemplary for the inner C-arm 220 with an arc length of at least 150 degrees (but preferably at least 180 degrees even where the gap is only 150 degrees) constructed as one unit within support C-arm 210 of this invention. As will be understood by those of skill in the art, a rotation around 360 degrees in that part of the coordinate system within which the inner C-arm 220 resides (within support C-arm 210) is feasible if the inner C-arm 220 is annularly extended throughout the entire 360 degrees.

Consequently, a 360 degree rotation of the X-ray source 230 and X-ray detector 240 is possible without moving the patient or utilizing and aligning secondary apparatus, as is the case with the '825 patent of the prior art. All gear rims and cogwheels, as well as the tapered ends, only serve to make travel by the inner C-arm upon a track formed within the support C-arm feasible. What should be perfectly clear is that the construction and functioning of any embodiment of the present invention is premised on the assumption that the inner C-arm 220, comprising an arc length of at least 150 degrees (that is, the length of the gap plus a sufficient overlap), must extend beyond the first end E1 of the support C-arm 210, over the 150 degree gap, and reenter the support C-arm at the entry (opposite) position on the opposite end of the support C-arm (E2).

Figure 4A:
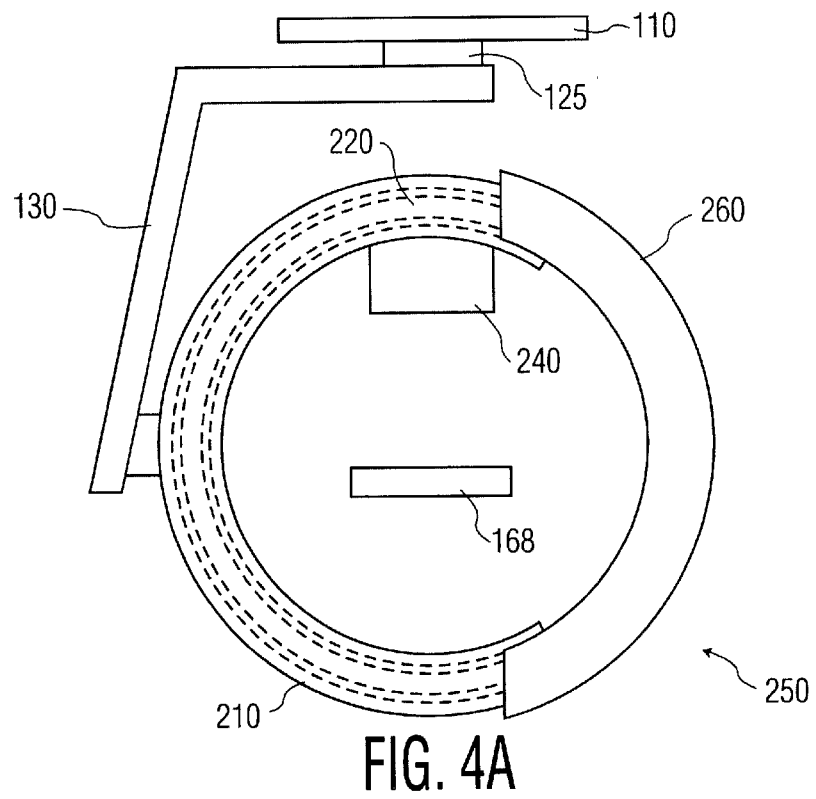
FIGS. 4A & 4B are schematic diagrams of an alternative embodiment of the C-arm X-ray system described below with reference to FIGS. 3A & 3B.
Figure 4B:
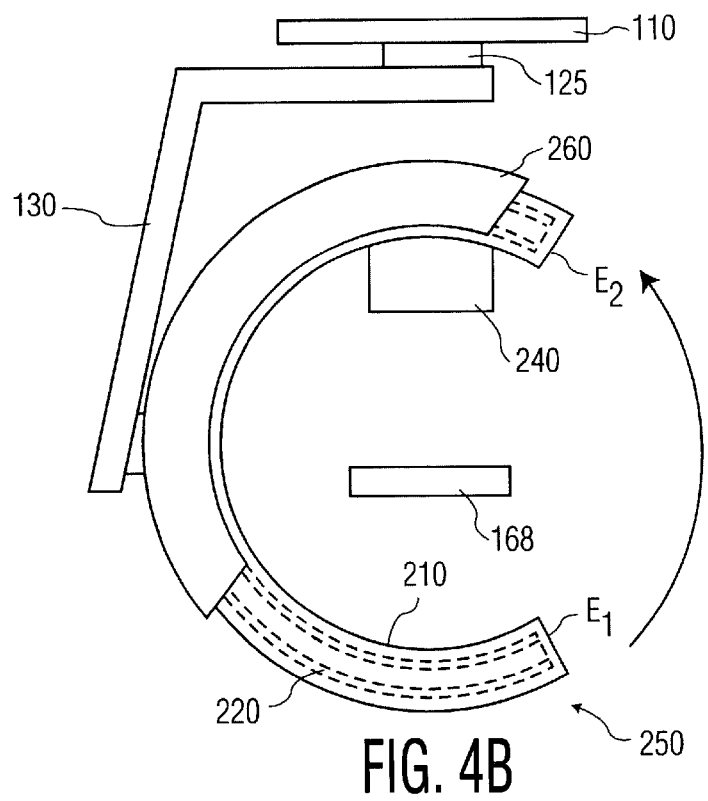

FIGS. 4A and 4B depict an alternative embodiment 250 of the C-arm X-ray system depicted in FIGS. 3A and 3B and described above. In this embodiment (FIGS. 4A and 4B), for reasons of safety, an extra protection part 260 having an arc length sufficient to overlap both ends of the support C-arm 210 (covering the gap) if necessary or desirable. The extra protection part 260 is mounted on the outside of the support C-arm 210 and is removable and slideable therealong.

Figure 5:
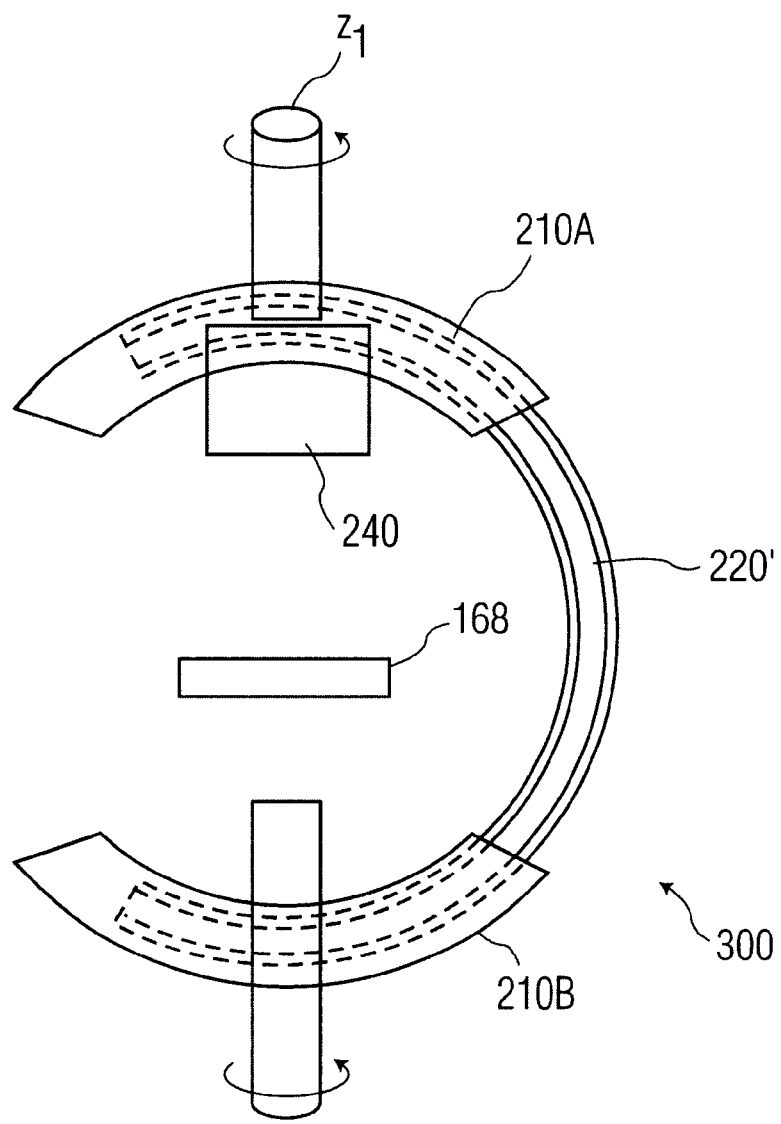
FIG. 5 is a schematic diagram of yet another alternative embodiment of the C-arm X-ray system of this invention.

FIG. 5 depicts yet another embodiment of a C-arm x-ray system 300 of this invention. In the FIG. 5 embodiment, the support C-arm is split up into two or more parts 210A and 210B, positioned at equal distances around the inner C-arm 220'. In such a construction, for example, the two support C-arms 210A and 210B could be placed on top and below the inner C-arm 220', respectively. C-arm part 210B could be positioned or affixed to a bearing equipment of sorts, and C-arm part 210A could be positioned or attached to the rail system or some other upper support platform.

The two or more partial C-arms would have a common axis of rotation identical to the symmetry axis Z1 as shown. The advantage of such a construction is increased patient accessibility while maintaining the functionality of the above-described embodiments of the invention. The reader should note, as one skilled in the art will understand, that the two partial C-arms 210A and 210B would require the same wheel/end/support arrangements mentioned above and to be discussed in sufficiently enabling detail below with respect to FIGS. 6A, 6B, 7.

FIGS. 6A, 6B show alternative embodiments of the various support mechanisms which allow the C-arm support (210, 210A or 210B) and inner C-arm (220 or 220') combination to operate according to the inventive principles herein. To drive (extend) the inner C-arm (220 or 220'), at least one driving wheel 310 is also constructed within the support C-arm (proximate each end). The inner C-arm 220' is driven upon gear rims 320 on its opposite sides which have contact with adjacent cogwheels 330 (FIG. 6A) fixed to the support C-arm. Each cogwheel 330 could be attached to a pair of smaller wheels 340 on the same axle 350. Alternatively, the common axle 350' (FIG. 6B) could be fixed to a spring arrangement 355 comprising springs 360, which spring arrangement would maintain the smaller wheels 340' at a small distance from a second pair of wheels 370.

The second pair of wheels 370 could then exert rotation on the first pair of wheels 340' and corresponding cogwheel 330'. This construction would provide an easy, simple small force engagement of the inner C-arm rims 320 and new cogwheel 330'.

The 310 part is meant to be exactly the same as 310'. We only left out the details (360/370) to keep the drawing simple. 310 and 310' represent the two bearing/force exertion arrangements on the opposite sides of 220. Maybe it would be less confusing to show only on side (e.g. the bottom one=FIG. 6B).

In a variation of the above-described embodiment shown in FIG. 7, additional suspension wheels 380 could be mounted on the ends of the support C-arm 210, attached to diverging arms 390 arranged in a funnel shape. An erroneous displacement of the inner C-arm 220" by any known or unknown force acting thereon could be accommodated (corrected). That is, FIG. 7 shows an alternative embodiment of the support ends of a C-arm X-ray system of the invention, where both ends of the inner C-arm 220" are tapered. Such tapering facilitates engagement of the inner and support C-arms. That is, all gear rims and cogwheels, as well as the tapered ends, only serve to make the exit/entry relative the support C-arm feasible.

Moreover, various other types of support end constructions may be considered for implementation within the inventive concepts comprising the present invention.

A single 360-degree rotation only would require the use of cables for interfacing the X-ray tube and detector. In multi-360 degree rotation systems, however, where there are several rotations of the gantry required for operation, slip rings should be included for interfacing the power support and the X-ray detector. However, in multi-360 degree rotation scanner, slip rings may be very cumbersome since leaving and reentering the contact is expected to cause electrical problems. To overcome these potential problems, an embodiment of the invention may comprise accumulators on the inner C for providing the required power. During resting position, the accumulators can automatically be recharged. The data are transferred to the reconstructer using a high-speed RF-link or optical link. The "reconstructor" is a separate computer collecting the projection data and using them to calculate the reconstructed attenuation volume matrix. Thus, it is an indispensable unit of the "scanner" but not considered as a necessary element in accordance with the definitions of the inventions disclosed within in this patent application.

And as an alternative to the high-speed data link, the data can be intermediately stored in data storage means included within the gantry during rotation and be transferred to the reconstructor in the resting position, as known to those skilled in the art. That is, accumulators, RF and optical links are primarily "off-the-shelf" technology items, the utilization and implementation of which will be known to those of skill in the art.

What is claimed is:

1. A C-arm X-ray system, comprising:
   an X-ray source;
   an X-ray detector; and
   a support C-arm construction including a support C-arm and an inner C-arm upon which the X-ray source and the X-ray detector are oppositely disposed, wherein the inner C-am, is disposed within the support C-arm and suspended upon at least one wheel construction disposed in the support C-arm;
   wherein the inner C-arm may be automatically driven annularly outside of a first end of the support C-arm from within the support C-arm and into a second end of the support C-arm to within the support C-arm thereby closing the a gap between the first and second ends of the support C-arm and allowing the X-ray source and X-ray detector to rotate a full 360 degrees for performing both fluoroscopic and CT procedures without moving a patient under examination, and/or reconstructing system components.

2. The C-arm X-ray system defined by claim 1, further comprising bearing equipment attached to the support C-arm.

3. The C-arm X-ray system defined by claim 1, further comprising a slideable cover disposed outside of the support C-arm and adapted for covering the inner C-arm when the slideable cover is extended to completely cover the gap during continuous rotation of the inner C-arm.

4. The C-arm X-ray system defined by claim 1, wherein the support C-arm comprises at least two separate partial support C-arms having a common axis of rotation.

5. The C-arm X-ray system defined by claim 4, wherein said at least two separate partial support C-arms are equal in length.

6. The C-arm X-ray device defined by claim 1, further comprising a support mechanism for supporting the inner C-arm within the support C-arm.

7. The C-arm X-ray system defined by claim 6, wherein at least a first end of the inner C-arm is tapered and at least a corresponding end of the support C-arm is funnel-shaped, the funnel-shaped end of the support C-arm adapted for receiving the first tapered end of the inner C-arm.

8. The support C-arm defined by claim 6, wherein the support mechanism includes at least one driving wheel.

9. The C-arm X-ray system defined by claim 6, wherein the inner C-arm includes gear rims and the support C-arm includes at least one cogwheel.

10. The C-arm X-ray system defined by claim 9, wherein said at least one cogwheel is attached to a pair of smaller wheels on one axle.

11. The C-arm X-ray system defined by claim 10, wherein said axle is affixed to a spring arrangement for maintaining the at least one cogwheel at an effective distance from a second pair of wheels.

12. A C-arm X-ray system, comprising:
    an X-ray source;
    an X-ray detector; and
    a support C-arm and an inner C-arm upon which the X-ray source and the X-ray detector are oppositely disposed, wherein the inner C-arm is constructed within the support C-arm and suspended upon at least one wheel construction disposed in the support C-arm such that the inner C-arm may be automatically driven annularly outside a first end of the support C-arm from within the support C-arm and into a second end of the support C-arm to within the support C-cam thereby closing a gap between the first and second ends of the support C-arm to form a closed ring, said at least one wheel construction allowing the inner C-arm to continuously rotate 360 degrees periodically.

13. The C-arm X-ray system defined by claim 12, wherein the X-ray source and X-ray detector are mounted on the inner C-arm.

14. The C-arm X-ray system defined by claim 12, wherein the X-ray source and X-ray detector rotate at least 360 degrees to perform both fluoroscopic and CT procedures without moving a patient under examination, and/or reconstructing system components.

15. The C-arm X-rays system defined by claim 12, wherein the x-ray detector and X-ray source are mounted on the inner C-arm approximately 180 degrees apart.

* * * * *